United States Patent
Perouse

[11] Patent Number: 5,843,189
[45] Date of Patent: Dec. 1, 1998

[54] BREAST PROSTHESIS

[75] Inventor: Eric Raul Perouse, L'Isle Adam, France

[73] Assignee: Laboratoire Perouse Implant, Bornel, France

[21] Appl. No.: 776,950

[22] PCT Filed: Jun. 11, 1996

[86] PCT No.: PCT/FR96/00881

§ 371 Date: Apr. 21, 1997

§ 102(e) Date: Apr. 21, 1997

[87] PCT Pub. No.: WO96/41593

PCT Pub. Date: Dec. 27, 1996

[30] Foreign Application Priority Data

Jun. 13, 1995 [FR] France .................................. 95 06996

[51] Int. Cl.⁶ ............................................. A61F 2/12
[52] U.S. Cl. ............................................ 623/8; 623/7
[58] Field of Search ........................... 623/7, 8, 17, 11

[56] References Cited

U.S. PATENT DOCUMENTS

| | | |
|---|---|---|
| 3,095,877 | 7/1963 | Rowan . |
| 3,986,213 | 10/1976 | Lynch . |
| 4,773,909 | 9/1988 | Chaglassian ............................... 623/8 |
| 5,246,454 | 9/1993 | Peterson ..................................... 623/8 |
| 5,447,535 | 9/1995 | Muller ........................................ 623/8 |
| 5,534,023 | 7/1996 | Henley ....................................... 623/8 |
| 5,549,671 | 8/1996 | Waybright et al. ........................ 623/8 |

FOREIGN PATENT DOCUMENTS

| | | |
|---|---|---|
| 322 194 | 7/1989 | European Pat. Off. . |
| 422 302 | 4/1991 | European Pat. Off. . |

*Primary Examiner*—Debra S. Brittingham
*Attorney, Agent, or Firm*—Wenderoth, Lind & Ponack, L.L.P.

[57] ABSTRACT

A breast implant comprising a plurality of bags filled with a fluid and each having, when at rest, a predetermined configuration. Each of the bags is defined by a flexible membrane. A means, particularly an outer shell, is provided to hold the bags together.

15 Claims, 4 Drawing Sheets

BREAST PROSTHESIS

BACKGROUND OF THE INVENTION

The present invention relates to a breast prosthesis. It relates also to a method for manufacture of such a prosthesis.

Breast prostheses are known which are designed to be implanted under the skin as a replacement for the mammary gland following its removal.

These prostheses are made up of an elastomeric envelope delimiting a hermetically closed space which is filled with a silicone gel or physiological serum.

Silicone gels reproduce the appearance and consistency of the natural mammary gland fairly well, but they are sometimes regarded unfavorably by public opinion.

Physiological serum poses a reduced risk to the patient, but its substantial fluidity does not permit good aesthetic characteristics of the prosthesis to be achieved. In particular, the considerable mobility of the physiological serum inside the envelope causes abrupt deformations of the prosthesis and is the origin of disconcerting noises.

Solutions which have been proposed to reduce the mobility of the physiological serum filler consist in arranging an open-cell foam in the envelope. Such foams, consisting of a silicone elastomer, are particularly difficult to produce and, in addition, they lack dimensional stability over the course of time. Furthermore, the random network of the cells in a foam and of the communicating passages does not allow the mechanical properties of the prosthesis to be defined as one would wish.

SUMMARY OF THE INVENTION

The object of the invention is to propose a breast prosthesis which has mechanical properties close to those of a natural mammary gland, does not have the disadvantages mentioned hereinabove, and permits in particular the use of physiological serum as the filling fluid.

To this end, the subject of the invention is a breast prosthesis characterized in that it includes a plurality of pockets which are filled with a fluid and which each have, at rest, a predetermined configuration, each pocket being delimited by a flexible membrane, and means which hold the pockets against one another.

The invention can have one or more of the following characteristics:

the membranes of the pockets in mutual contact adhere to one another;

the means for supporting the pockets include a flexible outer envelope in which the pockets are contained;

the envelope is hermetically closed and the space comprised between it and the pockets is filled with fluid;

the pockets are all substantially identical;

the pockets have a substantially spherical shape;

the pockets have an elongate shape and are rolled up on themselves;

each pocket is hermetically closed;

the pockets are made integral with one another so as to form one or more strings of closed pockets;

each pocket is equipped with at least one calibrated opening for circulation of the fluid;

the pockets are connected to one another by way of fine conduits connecting their circulation openings so as to form one or more strings of communicating pockets;

the strings of communicating pockets are open at their end;

the pockets and the conduits of the same string are delimited by the same membrane;

the strings are rolled up on themselves;

the membranes are made of silicone elastomer; and the filling fluid is physiological serum.

The invention relates also to a method for manufacture of a breast prosthesis in which the pockets are made integral with one another so as to form one or more strings of closed pockets, characterized in that it includes the following steps:

a) a tubing of elastomer filled with the fluid is extruded;

b) the tubing is passed between two press rollers equipped with crushing teeth so as to form strings consisting of hermetically closed pockets in the non-crushed zones, connected by flexible links in the crushed zones; and c) means (10) are used which hold the pockets thus formed against one another.

Moreover, the invention relates to a method for manufacture of a breast prosthesis in which the pockets are connected to one another by way of fine conduits connecting their circulation openings so as to form one or more strings of communicating pockets, characterized in that it includes the following steps:

a) a tubing of elastomer is extruded, b) a calibrated pipe is placed axially in the tubing, c) the tubing and the pipe are passed between two press rollers equipped with crushing teeth so as to form strings consisting of fine conduits in the crushed zones and pockets, communicating with one another via these conduits, in the non-crushed zones, d) means are used which hold the pockets thus formed against one another, and e) the pockets are filled with fluid.

The invention relates also to another method for manufacture of a breast prosthesis in which the pockets are connected to one another by way of fine conduits connecting their circulation openings so as to form one or more strings of communicating pockets, characterized in that it includes the following steps:

a) a tubing of elastomer is extruded, b) strings are formed by blowing so as to obtain pockets which are connected to one another by way of fine conduits, c) means are used which hold the pockets thus formed against one another, and d) the pockets are filled with fluid.

The methods can present one or more of the following characteristics:

after the step involving formation of the pockets, the membrane of these pockets is partially crosslinked;

at the step involving positioning of the means which hold the pockets, the strings are rolled up in a cavity of a mold having essentially the dimensions of the prosthesis, then the pockets of the strings are crosslinked in order to ensure that they are held in contact against one another.

BRIEF DESCRIPTION OF THE DRAWINGS

The invention will be better understood from reading the following description which is given solely by way of example and with reference to the attached drawings, in which.

Figure 1:
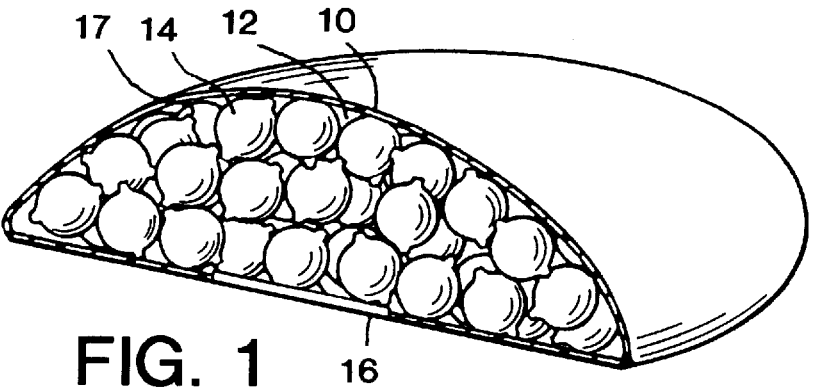
FIG. 1 is a perspective cross-sectional view of a breast prosthesis according to a first embodiment of the invention.

The prosthesis represented in FIG. 1 includes an outer envelope 10 delimiting a hermetically closed space 12 filled with physiological serum, and in which open pockets 14 are received.

The envelope 10 is formed by a flexible membrane of silicone elastomer reproducing substantially the shape of a mammary gland. It is closed off by a sealing disc 16.

In the embodiment in FIG. 1, the pockets 14, which are all identical, have a substantially spherical shape. They are delimited by a flexible membrane made of crosslinked silicone elastomer. Each pocket has a predetermined configuration at rest. The membrane of each pocket includes two calibrated openings 17 for circulation of the fluid. These openings 17 are diametrally opposite.

The pockets 14 fill the envelope 10 completely. They are held in contact against one another by the envelope 10 and thus form a coherent mass.

The physiological serum completely fills each pocket 14 and the space 12 comprised between the envelope 10 and the pockets 14.

The flexible membrane of each pocket can deform elastically when it is compressed, and can resume a substantially spherical shape in the absence of load. During these deformations, the fluid circulates with a contracting effect through the openings 17.

Figure 2:
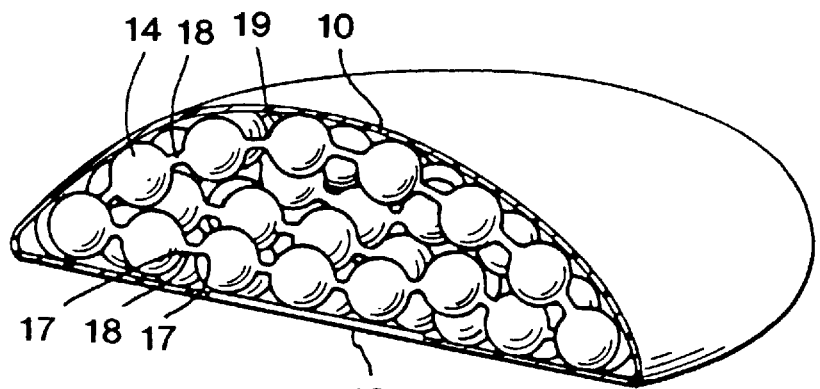
FIG. 2 is a similar view of a breast prosthesis according to a second embodiment.

Alternatively, as is represented in FIG. 2, the pockets 14 contained in the envelope 10 are connected to one another by way of fine calibrated conduits 18 which connect the circulation openings 17. The pockets 14 thus connected then form strings 19. These strings 19, which include, for example, about fifty pockets each, are rolled or coiled up on themselves inside the envelope 10.

The strings 19, totally filled with physiological serum, can be closed at their ends or left open. In the latter case, the space comprised between the strings 19 and the envelope 10 must be filled totally with physiological serum, whereas this is optional in the former case.

Figure 3:
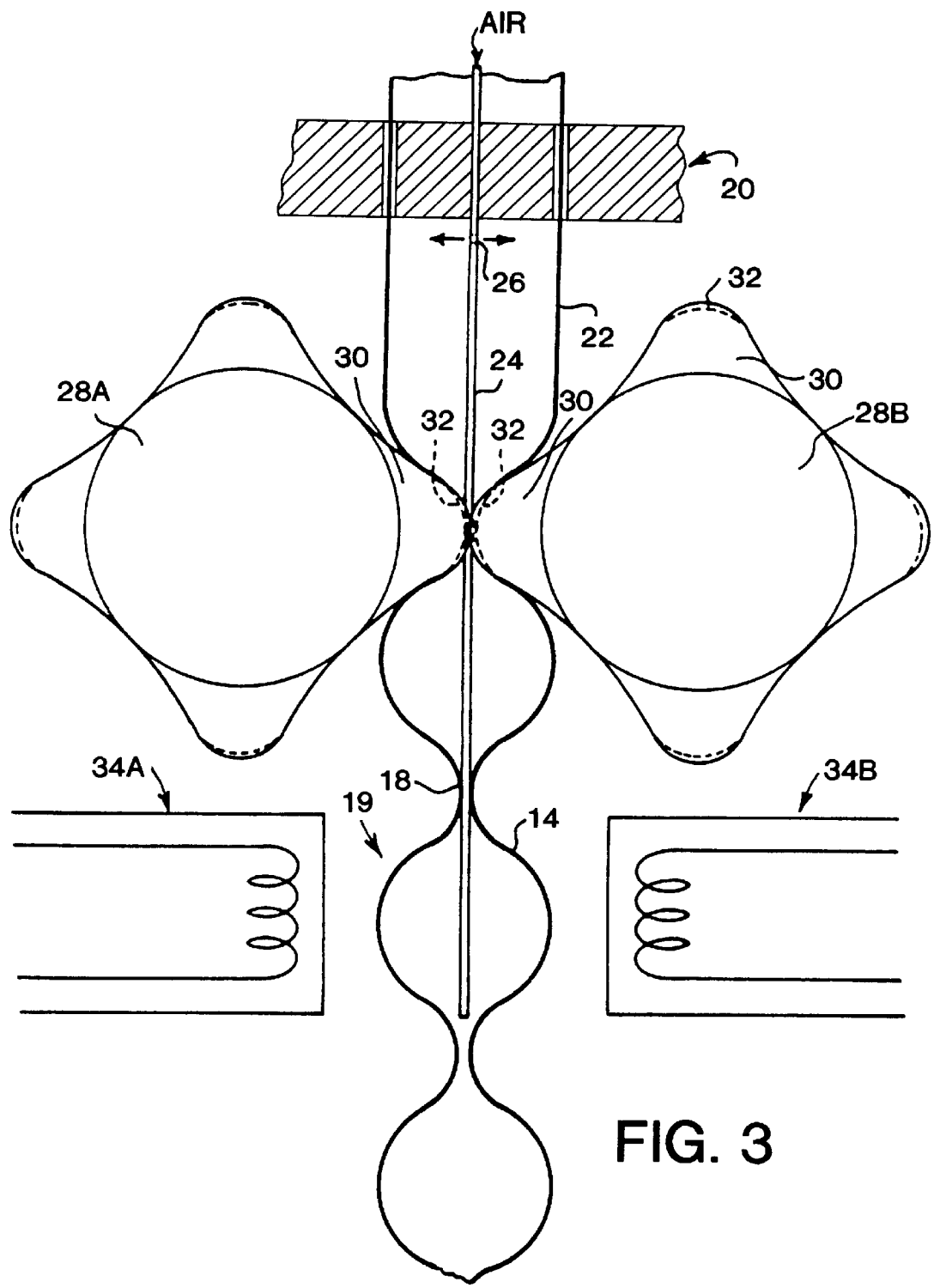
FIG. 3 is a diagrammatic cross-sectional view of an installation for manufacture of strings used in the breast prosthesis in FIG. 2.

An installation or apparatus permitting the production of such strings has been represented in FIG. 3. It includes an extrusion head 20 designed to form a flexible vertical tubing 22 whose rigid wall is a membrane of silicone elastomer. A rigid pipe 24 for air supply passes through the extrusion head 20 and extends vertically along the axis of the tubing 22. The pipe 24 is made of Teflon, for example, and has a calibrated external diameter corresponding to the desired diameter of the openings 17. Lateral vents 26 formed on the pipe just downstream of the extrusion head 20 permit delivery of the air to the inside of the tubing 22 so as to maintain the latter in a substantially cylindrical dilated shape.

Two synchronized press rollers 28A, 28B are arranged on either side of the pipe 24. These press rollers are each equipped with four teeth 30 for crushing the tubing 24. These teeth present a longitudinal groove 32 designed to enclose the pipe 24 between the teeth and thus to form, by pinching the tubing 24, the calibrated fine conduits 18 in the crushed zones. The non-crushed zones delimit the pockets 14 communicating with one another.

Alternatively, the strings can be obtained by extrusion blow-moulding, in a manner known per se. This suppresses any pinching flaw between the pockets 14.

Heating elements, in particular infrared radiation members 34A, 34B are arranged on either side of the pipe 24 downstream of, and therefore below, the press rollers 28A, 28B. They are designed to heat the string 19 and thus partially crosslink the latter. This partial crosslinking of the elastomer permits the fine conduits 18 to retain their shape after they are disengaged from the pipe 24.

Figure 4:
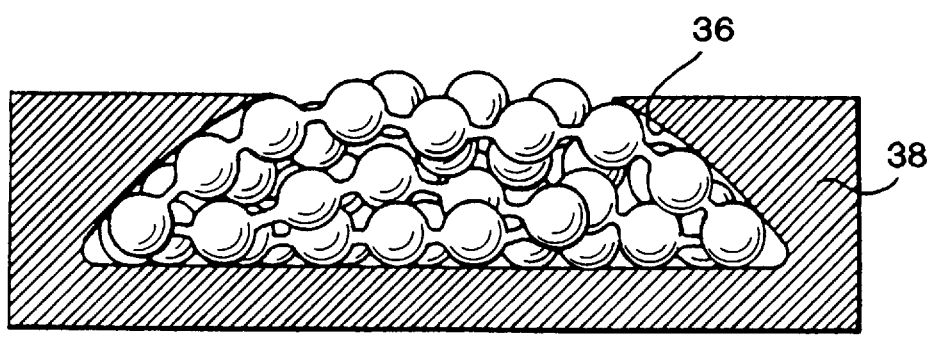
FIG. 4 is a cross-sectional view of a mold for the manufacture of a breast prosthesis.

In order to form a coherent mass starting from the strings produced by the installation in FIG. 3, these strings are rolled up inside a cavity 36 of a mold 38, represented in FIG. 4. The cavity 36 substantially reproduces the shape of the pocket 10 and is open on its upper face.

After complete filling of the mold 34, the latter is heated. Under the effect of the heat, the elastomer membrane of the string is crosslinked. Depending on the degree of preliminary crosslinking in the preceding step, the pockets in mutual contact can thus be firmly bonded to one another, bonded at points to one another, or left free.

The cohesion of the strings can also be obtained by adhesive bonding.

When the cohesion of the various strings is substantial, the envelope 10 may prove superfluous, and the breast prosthesis is formed solely by the network or the strings agglomerated and filled with physiological serum. In this case, the end of the strings is closed. However, in order to improve the surface quality of the prosthesis, it is possible to surround the strings with an envelope 10, not necessarily sealed.

In another variant in which an envelope 10 is used, the network of strings, configured in the mold 36, is introduced into it via the opening of the envelope. The envelope 10 and the network of strings are then filled totally with physiological serum. The sealing disc 16 is then put into place and sealed in order to ensure the leaktightness of the internal space delimited by the envelope 10. Any air bubbles trapped inside the envelope 10 are aspirated off with the aid of a syringe combined with a needle passing through the wall. The orifice resulting from the passage of the needle is then stopped using a drop of suitable adhesive.

According to one variant, the strings can be rolled up directly in the envelope 10 without having been joined to one another beforehand. They are then free to slide in the envelope 10 and they are held in contact with one another by the wall of the envelope.

In order to produce the prosthesis in FIG. 1, the individual pockets 14 are obtained starting from a string which is divided at the level of the conduits 18, or they are produced independently of one another. The independent pockets thus formed are then introduced into the envelope 10. As before, the pockets can be joined to one another more or less firmly by preliminary cross-linking of the material from which they are made, prior to shaping of the assembly of pockets, or they are left free.

It will be appreciated that a breast prosthesis such as described above slows down the circulation of the physiological serum inside it. In particular, the circulation can be controlled by suitable choice of the diameter of the conduits 18, the size of the pockets 14, the length of the strings, the number of pockets constituting the strings, and the presence or absence of open passages at the ends of the strings.

Thus, the ratio of the diameter of the conduits 18 to the diameter of the pockets 14 can be modified as a function of the mechanical characteristics which are sought.

Figure 5A:
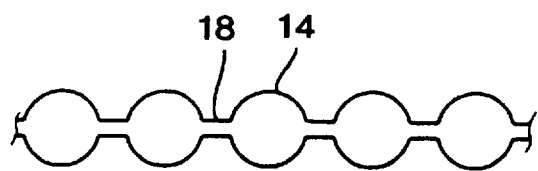
FIGS. 5A to 5D are views, in longitudinal section, of a segment of the string of communicating pockets according to alternative embodiments thereof.
Figure 5B:
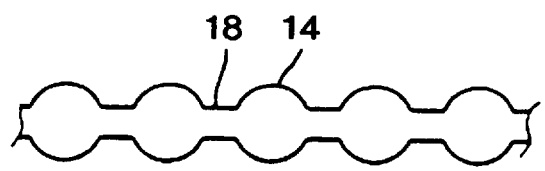
Figure 5C:
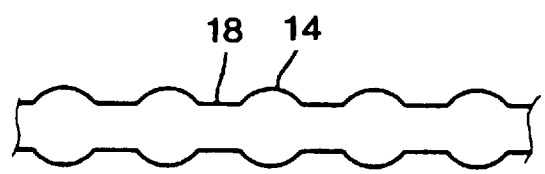

Examples of strings including conduits of increasing diameters are represented in FIGS. 5A to 5C.

Figure 5D:
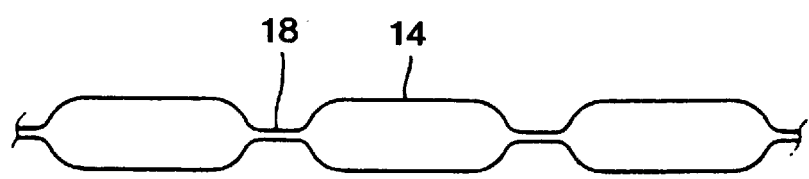

Furthermore, the pockets of the strings can have any shape configuration possible, for example elongate cylinders running along the length of the string, such as is represented in FIG. 5D. The diameter and the length of these cylinders are chosen so as to obtain the characteristics which are sought.

Alternatively, the pockets can be delimited by a flexible membrane which does not include a calibrated opening for circulation of the fluid. In this case, the pockets are hermetically closed and the fluid is maintained constantly inside these pockets. The deformation of the prosthesis is then obtained by movement of the fluid inside each pocket. This movement is rendered possible by the elasticity of the membrane forming the pockets, which permits a deformation of the latter.

Figure 6:
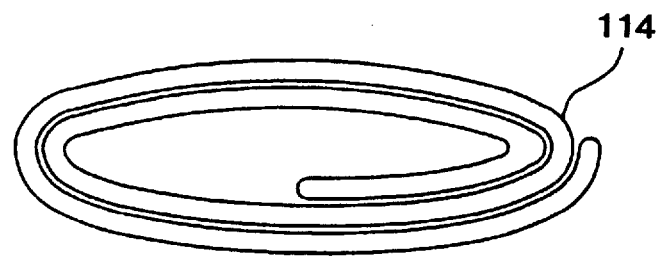
FIG. 6 is a sectional view of a closed elongate pocket rolled up on itself and used in an alternative embodiment of the breast prosthesis.

The closed pockets can be independent and of elongate shape, such as the pocket 114 represented in FIG. 6. In this case, in order to form the breast prosthesis, several pockets 114 are rolled up on themselves inside a support envelope, or they are adhesively bonded to one another. Independent and elongate pockets of this kind can of course also be equipped with openings for circulation of fluid, particularly at their ends.

Figure 7A:
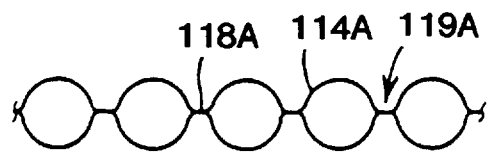
FIGS. 7A and 7B are views, in longitudinal section, of two alternative forms of segments of the string of closed pockets.
Figure 7B:
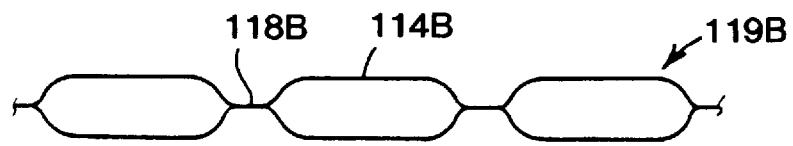

FIGS. 7A and 7B represent segments of strings 119A, 119B made up of flexible and closed pockets 114A, 114B which are designed to receive filling fluid. The strings 119A, 119B form breast prostheses by being rolled up.

In these figures, the pockets 114A, 114B are made integral with one another and they are connected via flattened, flexible links 118A, 118B.

These strings are obtained starting from an extruded elastomer tubing which can be crosslinked in the cold, is filled with the filling fluid, and has been crushed in localized zones in an installation which is substantially identical to that in FIG. 3, but whose pipe 24 does not extend between the rollers 28A, 28B, and in which the teeth 30 are not equipped with a longitudinal groove 32.

Under these conditions, it will be appreciated that the tubing passing between the rollers is crushed totally in certain localized zones in order to form the links 118A, 118B between which the closed pockets 114A, 114B are formed.

Depending on the diameter of the rollers and on the number of teeth, it is possible to determine the length of the pockets 114A, 114B.

In FIG. 7A, the pockets 114A have a substantially spherical shape, whereas in FIG. 7B the pockets 114B have the shape of an elongate cylinder along the length of the string 119B.

In another alternative embodiment of the breast prosthesis in which the pockets are closed, they are filled individually with the aid of a syringe or any other suitable means, prior to using the means which hold the pockets against one another. A drop of adhesive is used to close each orifice created by the passage of the needle of the syringe.

Irrespective of the embodiment, the control of the movements of fluid inside the breast prosthesis makes it possible to absorb the deformations thereof, and thus to reproduce relatively faithfully the mechanical properties and the consistency of the mammary gland, despite the use of a filling fluid such as physiological serum of very low viscosity.

However, other fluids can be used, oil for example, or other viscous solutions.

I claim:

1. A breast prosthesis comprising:
   a plurality of pockets filled with a liquid, wherein each of said pockets has, at rest, a predetermined configuration, and each of said pockets is delimited by a flexible membrane; and
   a holding device for holding said pockets against one another, wherein said pockets are formed integrally with one another so as to form at least one string.

2. The breast prosthesis as claimed in claim 1, wherein said flexible membranes of said pockets, which are held in mutual contact, adhere to one another.

3. The breast prosthesis as claimed in claim 1, wherein said holding device comprises a flexible outer envelope defining an interior space in which said pockets are contained.

4. The breast prosthesis as claimed in claim 3, wherein said flexible outer envelope is hermetically sealed and a portion of said interior space, defined between said flexible outer envelope and said pockets, is filled with a liquid.

5. The breast prosthesis as claimed in claim 1, wherein all of said pockets are substantially identical.

6. The breast prosthesis as claimed in claim 1, wherein each of said pockets has a substantially spherical shape.

7. The breast prosthesis as claimed in claim 1, wherein each of said pockets has an elongate shape, and said pockets are rolled up on themselves.

8. The breast prosthesis as claimed in claim 1, wherein each of said pockets is hermetically sealed.

9. The breast prosthesis as claimed in claim 1, wherein each of said pockets is equipped with at least one calibrated opening to permit circulation of said liquid.

10. The breast prosthesis as claimed in claim 9, wherein said pockets are connected to one another by a fine conduit connecting said circulation openings so as to form at least one string of communicating pockets.

11. The breast prosthesis as claimed in claim 10, wherein said flexible outer envelope is hermetically sealed and a portion of said interior space defined between said envelope and said pockets is filled with liquid, and said at least one string of communicating pockets has opposite ends which are open.

12. The breast prosthesis as claimed in claim 10, wherein said pockets and said conduits of said at least one string are delimited by the same flexible membrane.

13. The breast prosthesis as claimed in claim 1, wherein said at least one string comprises a plurality of strings which are rolled up on themselves.

14. The breast prosthesis as claimed in claim 1, wherein said flexible membranes of said pockets are made of silicone elastomer.

15. The breast prosthesis as claimed in claim 1, wherein said liquid comprises a physiological serum.

* * * * *